United States Patent [19]

Harada et al.

[11] Patent Number: 5,617,868
[45] Date of Patent: Apr. 8, 1997

[54] PULSE WAVE DETECTING APPARATUS

[75] Inventors: Chikao Harada, Komaki; Yuji Matsubara, Nagoya, both of Japan

[73] Assignee: Colin Corporation, Aichi-ken, Japan

[21] Appl. No.: 347,151

[22] Filed: Nov. 22, 1994

[51] Int. Cl.$^6$ ............................................. A61B 5/00
[52] U.S. Cl. .................... 128/672; 128/687; 128/690; 128/748
[58] Field of Search ................ 128/672, 687–90, 128/748

[56] References Cited

U.S. PATENT DOCUMENTS

| | | | |
|---|---|---|---|
| 4,976,268 | 12/1990 | Kurosawa et al. | 128/687 |
| 4,987,900 | 1/1991 | Eckerle et al. | 128/687 |
| 5,450,852 | 9/1995 | Archibald et al. | 128/687 |

FOREIGN PATENT DOCUMENTS

| | | | |
|---|---|---|---|
| 53-26437 | 8/1978 | Japan . | |
| 3-7139 | 1/1991 | Japan . | |
| 3-49957 | 3/1991 | Japan . | |
| 06178764 | 6/1994 | Japan | 125/687 |

*Primary Examiner*—Robert L. Nasser, Jr.
*Attorney, Agent, or Firm*—Oliff & Berridge

[57] ABSTRACT

An apparatus for detecting a pressure pulse wave produced from an arterial vessel of a living subject, including a pulse wave sensor including at least one pressure sensing element and having a press surface in which the pressure sensing element is provided, the press surface of the pulse wave sensor being adapted to be pressed against the arterial vessel of the subject via a body surface of the subject above the arterial vessel, so that the pressure sensing element detects the pressure pulse wave produced from the arterial vessel; a support member supporting the pulse wave sensor such that the pulse wave sensor is advanceable away from, and retractable toward, the support member, the support member being adapted to be worn on the subject such that the press surface of the pulse wave sensor is opposed to the body surface of the subject; and a polymer actuator provided between the support member and the pulse wave sensor, the polymer actuator producing a pressing force to press the pulse wave sensor against the arterial vessel of the subject via the body surface of the subject. The polymer actuator may be replaced by a piezoelectric actuator, a bimetal actuator, or a shape memory alloy actuator.

21 Claims, 6 Drawing Sheets

PULSE WAVE DETECTING APPARATUS

BACKGROUND OF THE INVENTION

1. Field of the Invention

The present invention relates to a pulse wave detecting apparatus including a pulse wave sensor and, in particular, to the art of pressing the pulse wave sensor on a body surface of a living subject.

2. Related Art Statement

There is known a pulse wave detecting apparatus including a pulse wave sensor having a press surface in which one or more pressure sensing elements are provided and which is adapted to be pressed against an artery of a living subject via the body surface or skin above the artery. The detecting apparatus detects, by the sensor, a pressure pulse wave produced from the artery of the subject. Usually, air pressure is utilized to press the pulse wave sensor on the body surface of the subject. One example is disclosed in Unexamined Japanese Patent Application (filed by the Assignee of the present application) laid open under Publication No. 3-7139. The disclosed pulse wave sensor is fixed to an outer face of a flexible diaphragm provided in a container-like housing such that the sensor is displaceable relative to the housing. When a pressurized air is supplied from an air pump via piping to a pressure chamber defined by the housing and the diaphragm, the diaphragm is inflated and accordingly the pulse wave sensor fixed to the diaphragm is advanced out of the housing so as to be pressed on the body surface of the living subject.

However, the above-mentioned conventional pulse wave detecting apparatus suffers from various problems resulting from the use of an air pump and a piping. In particular, in the case where the prior apparatus is used to detect a pulse wave from a living subject who is undergoing an exercise test or to monitor for a long period of time a pulse wave of a patient who is receiving medical treatments at his or her home, without restricting his or her daily activity, it has been proposed that the air pump be mounted on the housing, for preventing the piping from being stretched out and thereby moving the pulse wave sensor out of position on the subject, or for broadening the sphere of action of the patient. With this arrangement, however, the size and weight of a portion of the pulse wave detecting apparatus to be worn on a living subject, are enlarged and increased. Additionally, the noise of the air pump produced during operation thereof may disturb the sleeping of a living subject.

SUMMARY OF THE INVENTION

It is therefore an object of the present invention to provide a pulse wave detecting apparatus including a pulse wave sensor adapted to be pressed against an artery of a living subject via the body surface above the artery so as to detect a pressure pulse wave produced from the artery, wherein a portion of the apparatus to be worn on the subject includes an actuator which provides a pressing force to press the pulse wave sensor against the artery of the subject, nonetheless enjoys a small size and a light weight, and does not produce noise during operation of the actuator.

The above object has been achieved by the present invention. According to a first aspect of the present invention, there is provided an apparatus for detecting a pressure pulse wave produced from an arterial vessel of a living subject, comprising: a pulse wave sensor including at least one pressure sensing element and having a press surface in which the pressure sensing element is provided, the press surface of the pulse wave sensor being adapted to be pressed against the arterial vessel of the subject via a body surface of the subject above the arterial vessel, so that the pressure sensing element detects the pressure pulse wave produced from the arterial vessel; a support member supporting the pulse wave sensor such that the pulse wave sensor is advanceable away from, and retractable toward, the support member, the support member being adapted to be worn on the subject such that the press surface of the pulse wave sensor is opposed to the body surface of the subject; and a polymer actuator provided between the support member and the pulse wave sensor, the polymer actuator providing a pressing force to press the pulse wave sensor against the arterial vessel of the subject via the body surface of the subject.

In the pulse wave detecting apparatus constructed in accordance with the first aspect of the invention, a pulse wave sensor is supported by a support member adapted to be worn on the subject, such that the pulse wave sensor is displaceable relative to the support member and such that the press surface of the pulse wave sensor is opposite to the body surface of the subject, and a polymer actuator for pressing the pulse wave sensor is provided between the support member and the pulse wave sensor. While the polymer actuator is used to press the pulse wave sensor against the artery of the subject, the pulse wave sensor detects a pressure pulse wave produced from the artery of the subject. Since the polymer actuator may be provided with a smaller volume and a lighter weight than an air pump, a portion of the present apparatus to be worn on the subject enjoys a small size and a light weight as compared with the case where an air pump is incorporated into a to-be-worn portion of a conventional pulse wave detecting apparatus. Additionally, since the polymer actuator does not produce noise during operation thereof, the actuator does not disturb the sleeping of the subject.

According to a second aspect of the present invention, there is provided an apparatus for detecting a pressure pulse wave produced from an arterial vessel of a living subject, comprising: a pulse wave sensor including at least one pressure sensing element and having a press surface in which the pressure sensing element is provided, the press surface of the pulse wave sensor being adapted to be pressed against the arterial vessel of the subject via a body surface of the subject above the arterial vessel, so that the pressure sensing element detects the pressure pulse wave produced from the arterial vessel; a support member supporting the pulse wave sensor such that the pulse wave sensor is advanceable away from, and retractable toward, the support member, the support member being adapted to be worn on the subject such that the press surface of the pulse wave sensor is opposed to the body surface of the subject; and a piezoelectric actuator provided between the support member and the pulse wave sensor, the piezoelectric actuator providing a pressing force to press the pulse wave sensor against the arterial vessel of the subject via the body surface of the subject.

In the pulse wave detecting apparatus constructed in accordance with the second aspect of the invention, a pulse wave sensor is supported by a support member adapted to be worn on the subject, such that the pulse wave sensor is displaceable relative to the support member and such that the press surface of the pulse wave sensor is opposite to the body surface of the subject, and a piezoelectric actuator for pressing the pulse wave sensor is provided between the support member and the pulse wave sensor. While the piezoelectric actuator is used to press the pulse wave sensor against the artery of the subject, the pulse wave sensor detects a pressure pulse wave produced from the artery of the subject. Since the piezoelectric actuator may be provided with a smaller volume and a lighter weight than an air pump, a portion of the present apparatus to be worn on the subject enjoys a small size and a light weight as compared with the case where an air pump is incorporated into a to-be-worn portion of a conventional pulse wave detecting apparatus. Additionally, the piezoelectric actuator does not produce operational noise unlike the air pump. Thus, the present apparatus provides the same advantages as those of the apparatus in accordance with the first aspect of the invention.

According to a third aspect of the present invention, there is provided an apparatus for detecting a pressure pulse wave produced from an arterial vessel of a living subject, comprising: a pulse wave sensor including at least one pressure sensing element and having a press surface in which the pressure sensing element is provided, the press surface of the pulse wave sensor being adapted to be pressed against the arterial vessel of the subject via a body surface of the subject above the arterial vessel, so that the pressure sensing element detects the pressure pulse wave produced from the arterial vessel; a support member supporting the pulse wave sensor such that the pulse wave sensor is advanceable away from, and retractable toward, the support member, the support member being adapted to be worn on the subject such that the press surface of the pulse wave sensor is opposed to the body surface of the subject; and a bimetal actuator provided between the support member and the pulse wave sensor, the bimetal actuator providing a pressing force to press the pulse wave sensor against the arterial vessel of the subject via the body surface of the subject.

In the pulse wave detecting apparatus constructed in accordance with the third aspect of the invention, a pulse wave sensor is supported by a support member adapted to be worn on the subject, such that the pulse wave sensor is displaceable relative to the support member and such that the press surface of the pulse wave sensor is opposite to the body surface of the subject, and a bimetal actuator for pressing the pulse wave sensor is provided between the support member and the pulse wave sensor. While the bimetal actuator is used to press the pulse wave sensor against the artery of the subject, the pulse wave sensor detects a pressure pulse wave produced from the artery of the subject. Since the bimetal actuator may be provided with a smaller volume and a lighter weight than an air pump, a portion of the present apparatus to be worn on the subject enjoys a small size and a light weight as compared with the case where an air pump is incorporated into a to-be-worn portion of a conventional pulse wave detecting apparatus. Additionally, the bimetal actuator does not produce operational noise unlike the air pump. Thus, the present apparatus provides the same advantages as those of the apparatus in accordance with the first aspect of the invention.

According to a fourth aspect of the present invention, there is provided an apparatus for detecting a pressure pulse wave produced from an arterial vessel of a living subject, comprising: a pulse wave sensor including at least one pressure sensing element and having a press surface in which the pressure sensing element is provided, the press surface of the pulse wave sensor being adapted to be pressed against the arterial vessel of the subject via a body surface of the subject above the arterial vessel, so that the pressure sensing element detects the pressure pulse wave produced from the arterial vessel; a support member supporting the pulse wave sensor such that the pulse wave sensor is advanceable away from, and retractable toward, the support member, the support member being adapted to be worn on the subject such that the press surface of the pulse wave sensor is opposed to the body surface of the subject; and a shape memory alloy actuator provided between the support member and the pulse wave sensor, the shape memory alloy actuator providing a pressing force to press the pulse wave sensor against the arterial vessel of the subject via the body surface of the subject.

In the pulse wave detecting apparatus constructed in accordance with the fourth aspect of the invention, a pulse wave sensor is supported by a support member adapted to be worn on the subject, such that the pulse wave sensor is displaceable relative to the support member and such that the press surface of the pulse wave sensor is opposite to the body surface of the subject, and a shape memory alloy (SMA) actuator for pressing the pulse wave sensor is provided between the support member and the pulse wave sensor. While the SMA actuator is used to press the pulse wave sensor against the artery of the subject, the pulse wave sensor detects a pressure pulse wave produced from the artery of the subject. Since the SMA actuator may be provided with a smaller volume and a lighter weight than an air pump, a portion of the present apparatus to be worn on the subject enjoys a small size and a light weight as compared with the case where an air pump is incorporated into a to-be-worn portion of a conventional pulse wave detecting apparatus. Additionally, the SMA actuator does not produce operational noise unlike the air pump. Thus, the present apparatus provides the same advantages as those of the apparatus in accordance with the first aspect of the invention.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
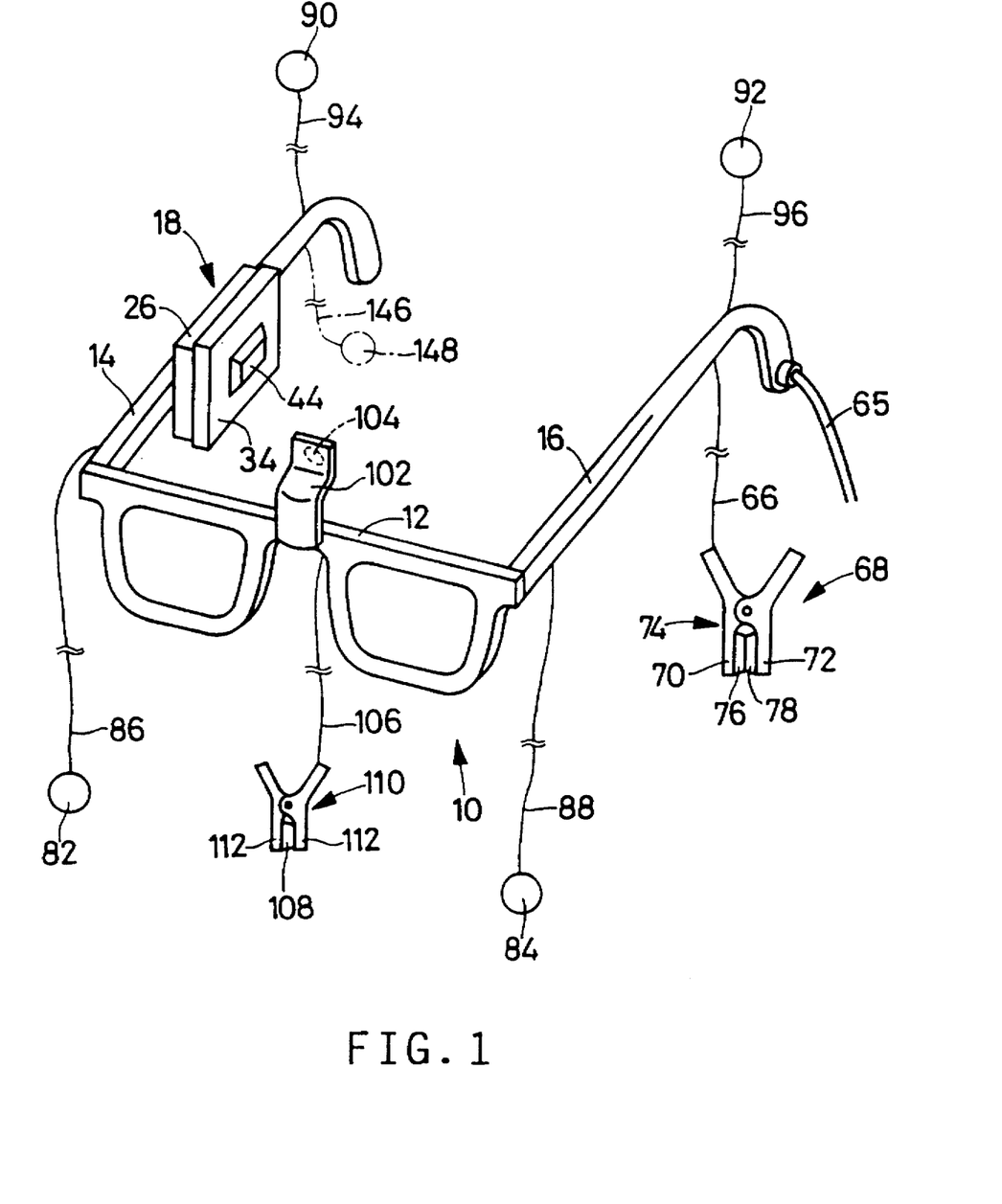
FIG. 1 is a perspective view of a lens frame which supports a pulse wave detecting apparatus (i.e., pulse wave detector probe 18) to which the present invention is applied.

Referring first to FIG. 1, there is shown a pulse wave detector probe 18 (hereinafter, abbreviated to the "PW probe") to which the present invention is applied. The detector probe 18 is attached to a first or right temple 14 of a lens frame 10. The lens frame 10 additionally includes a second or left temple 16 and a front rim 12 connecting the two temples 14, 16. The lens frame 10 is entirely formed of a resin. Various physical-information sensors (described later) including the PW probe 18 are mounted on the lens frame 10. The lens frame 10 and the various physical-information sensors are used for obtaining various sorts of physical information from a living subject such as a patient who is undergoing an exercise test such as walking.

Figure 2:
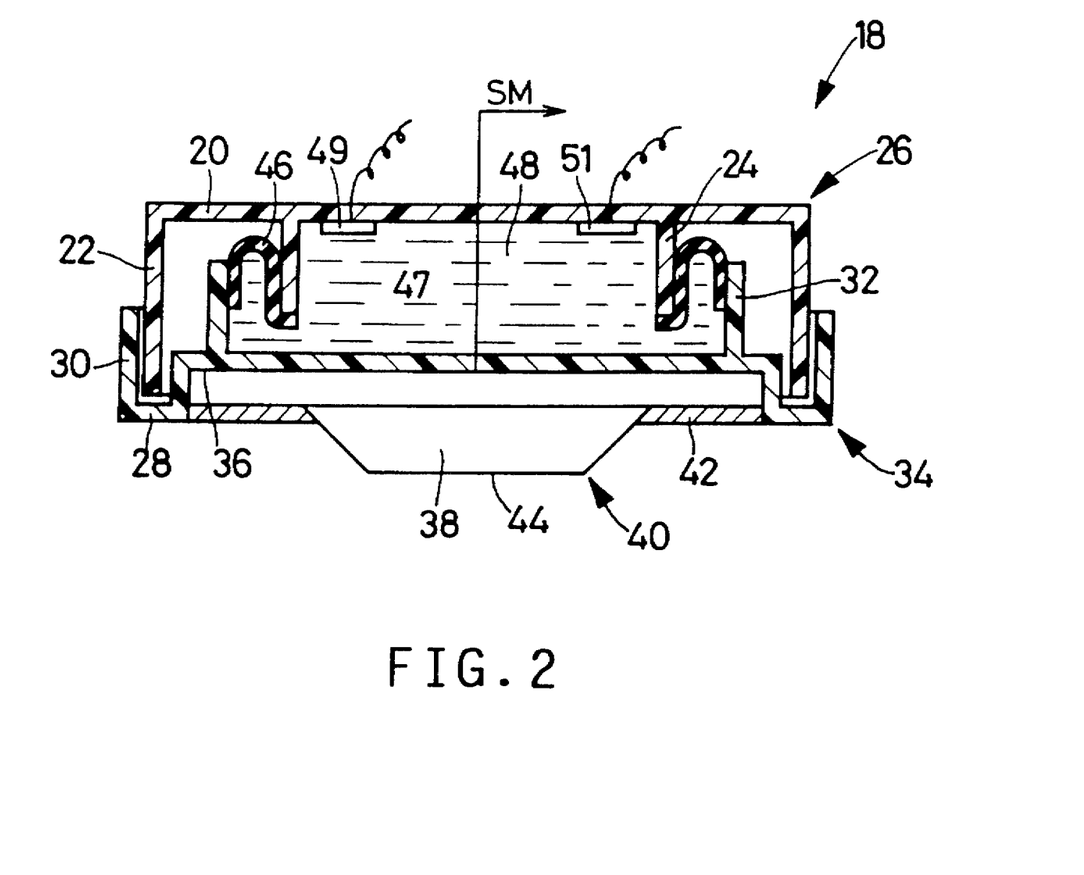
FIG. 2 is a cross-sectional view of the pulse wave detector probe 18 shown in FIG. 1.

The PW probe 18 fixed to an inner face of the first temple 14 detects a pressure pulse wave produced from a superficial temporal (ST) artery of the head of the patient in synchronism with heartbeat of the patient. As shown in FIGS. 1 and 2, the PW probe 18 includes a first housing 26 and a second housing 34, each formed of a resin. The first housing 26 has (a) a bottom wall 20 in the form of a rectangular plate, (b) a side wall 22 protruding from an outer periphery of the bottom wall 20, and (c) an intermediate wall 24 protruding from the bottom wall 20 and located inside the side wall 22. The first housing 26 is fixed at an outer surface of the bottom wall 20 to the first temple 14 of the lens frame 10. The second housing 34 has (d) a bottom wall 28 in the form of a rectangular plate, (e) a side wall 30 protruding from an outer periphery of the bottom wall 28, and (f) an intermediate wall 32 protruding from the bottom wall 28 and located inside the side wall 30. The first housing 26 is received in the second housing 34 such that the side wall 22 of the first housing 26 is positioned with a small clearance inside the side wall 30 of the second housing 34, and such that the intermediate wall 24 of the first housing 26 is positioned with a predetermined distance from the intermediate wall 32 of the second housing 34.

The second housing 34 has a recess 36 open in an outer surface of the bottom wall 28. A pulse wave (PW) sensor 40 fits in the recess 36, and a guard plate 42 prevents the PW sensor 40 from coming off the recess 36 of the second housing 34. The PW sensor 40 includes a mounded portion 38 protruding outward through a central opening of the guard plate 42. A top surface 44 of the mounded portion 38 of the PW sensor 40 provides a press surface adapted to be pressed against the ST artery of the patient via the skin directly above the artery. An array of pressure sensing elements (e.g., semiconductor pressure sensor elements, not shown) are provided in the press surface 44 of the PW sensor 40.

The first and second housings 26, 34 are connected to each other with a flexible diaphragm 46 which is formed of an elastic material such as a rubber and is provided between the respective intermediate walls 24, 32 of the two housings 26, 34. Thus, a closed space 47 is defined by the bottom and intermediate walls 20, 24 of the first housing 26, the bottom and intermediate walls 28, 32 of the second housing 34, and the elastic diaphragm 46. The second housing 34 and the PW sensor 40 fixed thereto are displaceable relative to, i.e., advanceable away from, and retractable toward, the first housing 26 as seen in vertical directions in FIG. 2.

The closed space 47 provided between the first and second housings 26, 34 is filled with a jelly of polymer gel 48. The polymer gel 48 may be a polymethacrylate gel containing fixed dimethylviologen groups. A pair of electrodes 49, 51 are provided on an inner surface of the bottom wall 20 of the first housing 26. When a direct current is applied to the polymer gel 48 via the electrodes 49, 51, the polymer gel 48 is expanded or contracted. The amount of expansion or contraction of the polymer gel 48 is controllable according to the directions and magnitudes of the electric current applied thereto. When the polymer gel 48 is expanded, the second housing 34 and the PW sensor 40 are advanced outward from the first housing 26, so that the press surface 44 of the mounded portion 38 of the PW sensor 40 is pressed against the ST artery of the patient via the skin above the artery. When the polymer gel 48 is contracted, the PW sensor 40 is released from the pressed contact with the patient's skin. In the present embodiment, the PW probe 18 corresponds to a pulse wave detecting apparatus; the first housing corresponds to a support member; and the polymer gel 48 corresponds to a polymer actuator.

Figure 3:
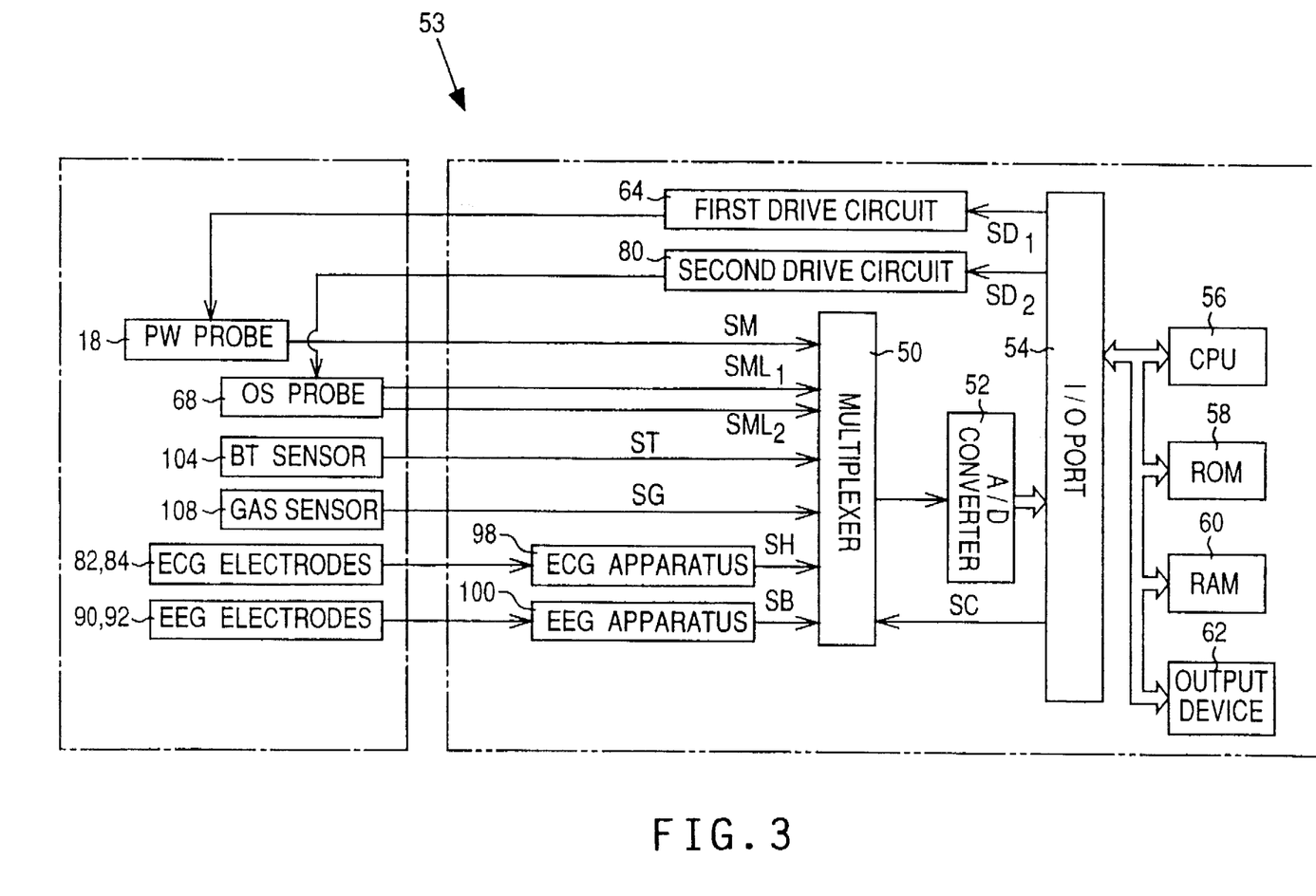
FIG. 3 is a diagrammatic view of a physical-information monitor system including the pulse wave detector probe 18 shown in FIG. 1.

The PW sensor 40 being pressed against the ST artery of the patient generates a pulse wave signal, SM, i.e., electric signal representing the detected pressure pulse wave produced from the ST artery in synchronism with heartbeat of the patient. The pulse wave signal SM is supplied to an input and output (I/O) port 54 via a multiplexer 50 and an analog to digital (A/D) converter 52, as shown in FIG. 3. The I/O port 54 is connected to a central processing unit (CPU) 56, a read only memory (ROM) 58, and a random access memory (RAM) 60, and an output device 62 via data bus lines. The CPU 56 processes input signals according to control programs pre-stored in the ROM 58 by utilizing a temporary-storage function of the RAM 60, and supplies a switch signal, SC, to the multiplexer 50 via the I/O port. 54 so as to place the multiplexer 50 in a desired one of selectable positions. Also, the CPU 56 supplies a first drive signal, SD1, to a first drive circuit 64 via the I/O port 54 so as to cause the drive circuit 64 to supply a direct current having a desired direction to the polymer gel 48 of the PW probe 18. In the latter case, the CPU 56 collects pulse wave signals SM while at the same time gradually changing magnitudes of the direct current supplied to the polymer gel 48 and thereby gradually changing amounts of expansion of the polymer gel 48, and determines based on the collected signals SM a magnitude of the direct current corresponding to an amount of expansion of the polymer gel 48 at which a portion of the wall of the ST artery is flattened under the PW sensor 40 pressed thereagainst by the expanded polymer gel 48. Then, the CPU 56 controls the first drive circuit 64 to supply the polymer gel 48 with the direct current having the thus determined magnitude. With the direct current being maintained at the determined magnitude, the CPU 56 reads in the pulse wave signal SM from the PW sensor 40, and controls the output device 62 to indicate the waveform of pressure pulse wave represented by the signal SM, on a display (e.g., cathode ray tube, not shown) and/or record the same on a record sheet (not shown). Respective lead wires of the electrodes 49, 51 and a lead wire (not shown) of the PW sensor 40 are embedded in the first temple 14, front rim 12, and second temple 16 of the lens frame 10, and finally enter a cable 65 which is connected to a free end of the second temple 16 opposite to the other end thereof on the side of the front rim 12. Thus, the electrodes 49, 51 and the pulse wave sensor 40 are connected to the I/O port 54.

Meanwhile, an oxygen saturation measure probe (OS probe) 68 is attached via a first lead wire 66 to the second temple 16 of the lens frame 10. The lead wire 66 passes the second temple 16 and enters the cable 65. Thus, the OS probe 68 is connected to the I/O port 54 via the cable 64. The OS probe 68 includes a clip 74 having a pair of pinching arms 70, 72, and a light emitter 76 and a light receiver 78 provided between, and supported by, the two arms 70, 72 such that the light receiver 78 is opposite to the light emitter 76. The OS probe 68 is worn on an ear lobe of the patient by pinching the lobe with the two arms 70, 72 of the clip 74 such that the lobe is sandwiched between the light emitter 76 and the light receiver 78. The light emitter 76 includes two light emitting elements (not shown) emitting a 630 nm wavelength light and a 900 nm wavelength light, respectively. The light receiver 78 includes two optical filters (not shown) which permit only the 630 nm and 900 nm wavelength lights to pass therethrough, respectively, and two light receiving elements which receive the two lights having passed through the two optical filters, respectively. The CPU 56 supplies a second drive signal, SD2, to a second drive circuit 80 via the I/O port 54 so as to cause the drive circuit 80 to drive the light emitter 76 and thereby emit the two lights toward the tissue of the ear lobe, so that the two light receiving elements of the light receiver 78 receives the two lights having passed through the ear lope and the two optical filters. The light receiver 78 generates two photoelectric pulse wave (PEPW) signals, SML1, SML2, representing the detected two lights, respectively. The two PEPW signals SML1, SML2 are supplied to the I/O port 54 via the multiplexer 50 and the A/D converter 52.

The CPU 56 determines a blood oxygen saturation of the patient based on the PEPW signals SML1, SML2 supplied to the I/O port 54, according to a known algorithm pre-stored in the ROM 58, and operates the output device 62 to display the determined oxygen saturation. The oxygen saturation determining method is disclosed in, e.g., Japanese Patent Application laid open for opposition purposes under Publication No. 53-26437. In short, the disclosed method is based on the principle that the ratio of a first absorption coefficient calculated from the first PEPW signal SML1 and a second absorption coefficient calculated from the second PEPW signal SML2 is directly proportional with a blood oxygen saturation. The CPU 56 calculates this ratio from the two signals SML1, SML2, and determines the oxygen saturation of the patient based on the thus calculated ratio according to a predetermined relationship between the ratio and the oxygen saturation which is pre-stored in the ROM 58.

Two electrocardiograph (ECG) electrodes 82, 84 adapted to be worn on the skin of the patient are attached via a second and a third lead wire 86, 88 to respective end portions of the two temples 14, 16 near to the front rim 12. In addition, two electroencephalograph (EEG) electrodes 90, 92 adapted to be worn on the skin of the head of the patient are attached via a fourth and a fifth lead wires 94, 96 to respective free end portions of the two temples 14, 16 distant from the front rim 12. The second and third lead wires 86, 88 pass through the lens frame 10 and goes into the cable 65, so that the ECG electrodes 82, 84 are connected via the cable 65 to an ECG apparatus 98. Meanwhile, the fourth and fifth lead wires 94, 96 pass through the lens frame 10 and enter the cable 65, so that the EEG electrodes 90, 92 are connected via the cable 65 to an EEG apparatus 100. The ECG apparatus 98 generates an electrocardiogram (ECG) signal, SH, representing an electrocardiogram waveform obtained from the patient through the ECG electrodes 82, 84, while the EEG apparatus 100 generates an electroencephalogram (EEG) signal, SB, representing an electroencephalogram waveform obtained from the patient through the EEG electrodes 90, 92. The two signals SH, SB are supplied to the I/O port 54 via the multiplexer 50 and the A/D converter 52.

The CPU 56 operates, according to a control program pre-stored in the ROM 58, the output device 62 to display the electrocardiogram waveform represented by the ECG signal SH supplied to the I/O port 54 and the electroencephalogram waveform represented by the EEG signal SB supplied to the same 54.

Furthermore, a plate member 102 is fixed to a front face of a central portion of the front rim 12. A body temperature (BT) sensor 104 such as a thermistor is attached to a rear face of the plate member 102 to measure a body temperature of the patient. The BT sensor 104 is adapted to contact the skin of the forehead of the patient. Moreover, a gas sensor 108 is attached via a sixth lead wire 106 to the central portion of the front rim 12. The gas sensor 108 measures a concentration of carbonic acid gas ($CO_2$) contained in the expirated gas of the patient. The gas sensor 108 is fixed to one of two pinching arms 112, 112 of a clip 110. The gas sensor 108 is worn on the patient by pinching the nose of the patient with the pinching arms 112, 112 of the clip 110 such that the gas sensor 108 is positioned inside a naris of the nose. A lead wire (not shown) of the BT sensor 104 and the sixth lead wire 106 of the gas sensor 108 pass through the lens frame 10 and enter the cable 65, so that the BT sensor 104 and the gas sensor 108 are connected via the cable 65 to the multiplexer 50. The BT sensor 104 generates a body temperature signal, ST, representing the measured body temperature of the patient, and the gas sensor 108 generates a gas concentration signal, SG, representing the measured $CO_2$ concentration. The two signals ST, SG are supplied to the I/O port 54 via the multiplexer 50 and the A/D converter 52.

The CPU 56 operates, according to a control program pre-stored in the ROM 58, the output device 62 to display the body temperature represented by the signal ST supplied to the I/O port 54 and the $CO_2$ concentration represented by the signal SG supplied to the same 54. In FIG. 3, all the elements enclosed by a one-dot chain line are mounted on the lens frame 10, while all the elements enclosed by a two-dot chain line are provided in a main housing (not shown) which is connected via the cable 65 to the lens frame 10 and which is adapted to be disposed away from the lens frame 10. Thus, FIG. 3 shows an electric arrangement of a physical-information monitor system 53 including the PW probe 18 as the pulse wave detecting apparatus.

It emerges from the foregoing description that in the present embodiment the PW sensor 40 of the PW probe 18 mounted on the lens frame 10 is pressed against the superficial temporal artery of the patient via the skin above the artery because of the expansion of the polymer gel 48 provided in the closed space 47 of the PW probe 18, so that the PW sensor 40 detects the pressure pulse wave produced from the artery in synchronism with the heartbeat of the patient. The polymer gel 48 is used with a smaller volume and a lighter weight than those of an air pump which has been employed in a conventional pulse wave detector probe. Thus, in the present embodiment, the PW probe 18 enjoys a smaller size and a lighter weight than a conventional probe using an air pump as a pulse wave sensor actuator.

Since the polymer gel 48 does not generate noise during operation thereof, unlike an air pump, the patient does not suffer from noise even if the PW probe 18 including the polymer gel 48 is worn on the head of the patient.

In the present embodiment, the various physical-information sensors 18, 68, 82, 84, 90, 92, 104, 108 are mounted on the lens frame 10, and the respective lead wires 66, 86, 88, 94, 96, 106 of those sensors are connected via the single cable 65 to the main housing (not shown) disposed away from the lens frame 10. The use of the single cable 65 effectively prevents the number of lead wires from being entwined with each other.

Since in the present embodiment the PW probe 18 is worn on the head of the patient that is less frequently moved than other body portions such as an upper arm or a forearm, the PW probe 18 is more effectively prevented from being moved out of position because of the physical motion of the patient, than a conventional PW probe adapted to be worn on, e.g., a wrist of a patient.

Furthermore, in the present embodiment, the PW sensor 40 detects the pressure pulse wave from the superficial temporal (ST) artery of the patient. Since the ST artery is near to the heart of the patient, the pressure pulse wave detected by the PW sensor 40 more advantageously reflects the current condition of the circulatory organ of the patient than a conventional PW probe adapted to detect a pressure pulse wave from other arteries such as a radial artery of a wrist of a patient, in particular in the event that the blood circulation of the patient is lowered.

Figure 4:
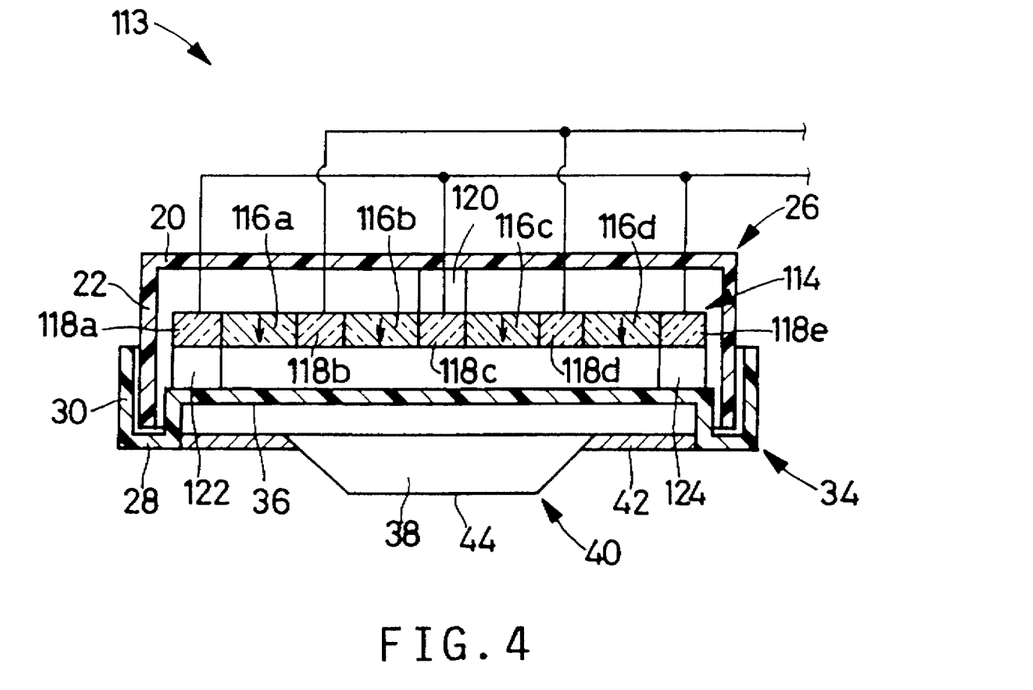
FIG. 4 is a cross-sectional view corresponding to FIG. 2, showing another pulse wave detector probe 113 as a second embodiment of the invention.
Figure 5:
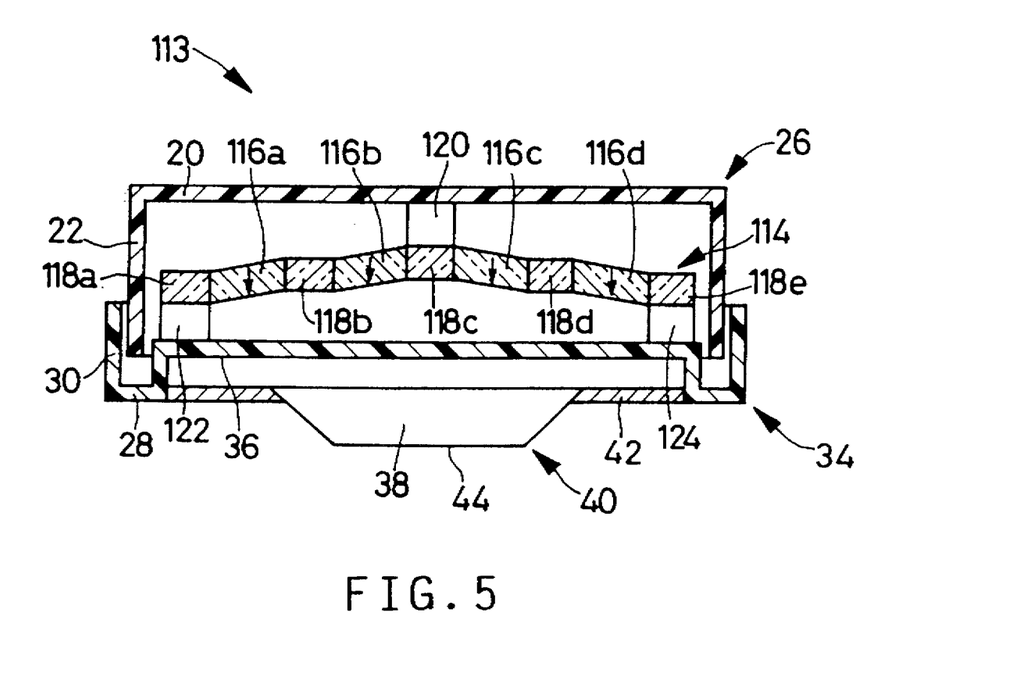
FIG. 5 is a view illustrating a pulse wave sensor 40 held in an advanced position thereof with a stacked piezoelectric ceramic element 114 being curved.

Referring next to FIGS. 4 and 5, there is shown a second embodiment of the present invention. The second embodiment relates to a pulse wave sensor probe (PW probe) 113. The same reference numerals as used in FIGS. 1 to 3 for the PW probe 18 as the first embodiment are used to designate the corresponding elements and parts of the PW probe 113 as the second embodiment, and the description of those elements and parts is omitted.

As shown in FIG. 4, the PW sensor 113 does not have parts corresponding to the intermediate walls 24, 32 of the PW sensor 18, and has a piezoelectric actuator in the form of a stacked piezoelectric ceramic element 114 in place of the polymer gel 48 of the PW sensor 18. The stacked piezoelectric ceramic element 114 used as the piezoelectric actuator is disclosed in, e.g., Unexamined Japanese Patent Application laid open under Publication No. 3-49957. The piezoelectric ceramic element 114 is obtained by alternately stacking (a) four piezoelectric ceramic layers 116a, 116b, 116c, 116d each of which is formed of lead titanate zirconate having ferroelectricity and which is polarized in a direction indicated at arrow in the figure; and (b) five semiconductor electrode layers 118a, 118b, 118c, 118d, 118e each of which is formed of barium titanate known as a thermistor material. The piezoelectric ceramic element 114 has a rectangular, plate-like configuration. The central electrode 118c of the piezoelectric element 114 is fixed via a first fixture 120 to a bottom wall 20 of a first housing 26, and the opposite end electrodes 118a, 118e are fixed via a second and a third fixture 122, 124 to a bottom wall 28 of a second housing 34.

When a drive current is applied between the electrodes 118a, 118c, 118e and the electrodes 118b, 118d of the piezoelectric element 114, each piezoelectric ceramic layer 116a, 116b, 116c, 116d is deformed because of slipping effect, as shown in FIG. 5. Consequently the piezoelectric element 114 as a whole is curved such that the end electrodes 118a, 118e become most distant from the bottom wall 20 of the first housing 26. The degree of curvature of the piezoelectric element 114 being driven, or distance of the end electrodes 118a, 118e from the bottom wall 20 of the first housing 26 can be controlled by changing the magnitudes of the drive current applied to the electrodes 118a to 118e. Since the second housing 34 and a pulse wave sensor (PW sensor) 40 fixed thereto are connected to the end electrodes 118a, 118e via the fixture members 122, 124, the PW sensor 40 can be pressed against a superficial temporal artery of a patient with an appropriate pressing force corresponding to the drive current applied to the electrodes 118a to 118e. When the drive current is disconnected from the electrodes 118a to 118e, the piezoelectric element 114 is restored to its original shape, i.e., becomes flat, so that the PW sensor 40 is retracted away from the patient. In the second embodiment, too, the stacked piezoelectric ceramic element 114 enjoys a small size and a light weight as compared with a conventional air pump, and does not produce operational noise unlike the air pump.

Figure 6:
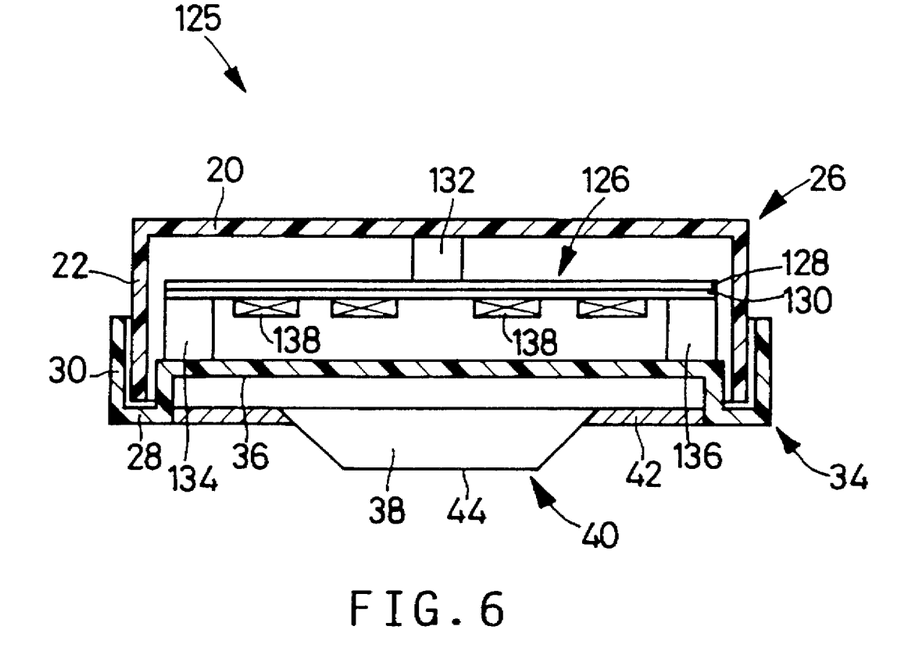
FIG. 6 is a cross-sectional view corresponding to FIG. 2, showing another pulse wave detector probe 125 as a third embodiment of the invention.

Referring next to FIG. 6, there is shown a third embodiment of the present invention. The third embodiment relates to a pulse wave sensor probe (PW probe) 125. The same reference numerals as used in FIGS. 1 to 3 for the PW probe 18 as the first embodiment are used to designate the corresponding elements and parts of the PW probe 125 as the third embodiment, and the description of those elements and parts is omitted.

The PW sensor 125 does not have parts corresponding to the intermediate walls 24, 32 of the PW sensor 18, and has a bimetal 126 in place of the polymer gel 48 of the PW sensor 18. The bimetal 126 includes a first and a second metal sheet 128, 130 which have different coefficients of thermal expansion and are adhered to each other. The first metal sheet 128 having a greater coefficient of thermal expansion is fixed at a central portion thereof to a first housing 26 via a first fixture 132 having a heat-insulating property, and the second metal sheet 130 having a smaller coefficient of thermal expansion is fixed at opposite end portions thereof to a second housing 34 via a second and a third fixture 134, 136 each having a heat-insulating property. Four Peltier modules 138 are fixed to a major surface of the second metal sheet 130 which is opposite to the first metal sheet 128. The four Peltier modules 138 are equidistant from each other at appropriate intervals. Each Peltier module 138 is obtained by sandwiching a plurality of p-n semiconductor devices between a pair of ceramic plates. Each p-n semiconductor device is obtained by jointing a p-type semiconductor and an n-type semiconductor via a metal sheet. Each Peltier module 138 functions as a semiconductor heating device, and a semiconductor cooling device, depending upon the directions of an electric current applied thereto. When the Peltier modules 138 are heated, the bimetal 126 is curved. The degree of curvature of the bimetal 126 is controllable by changing the amounts of electricity supplied to the Peltier modules 138. Since a second housing 34 and a pulse wave sensor (PW sensor) 40 fixed thereto are connected to the opposite end portions of the bimetal 126 via the fixture members 134, 136, the PW sensor 40 can be pressed against a superficial temporal artery of a patient with an appropriate pressing force corresponding to the electric current applied to the bimetal 126. In the third embodiment, too, an actuator provided by the bimetal 126 and the Peltier modules 138 enjoys a small size and a light weight as compared with a conventional air pump, and does not produce operational noise unlike the air pump.

Figure 7:
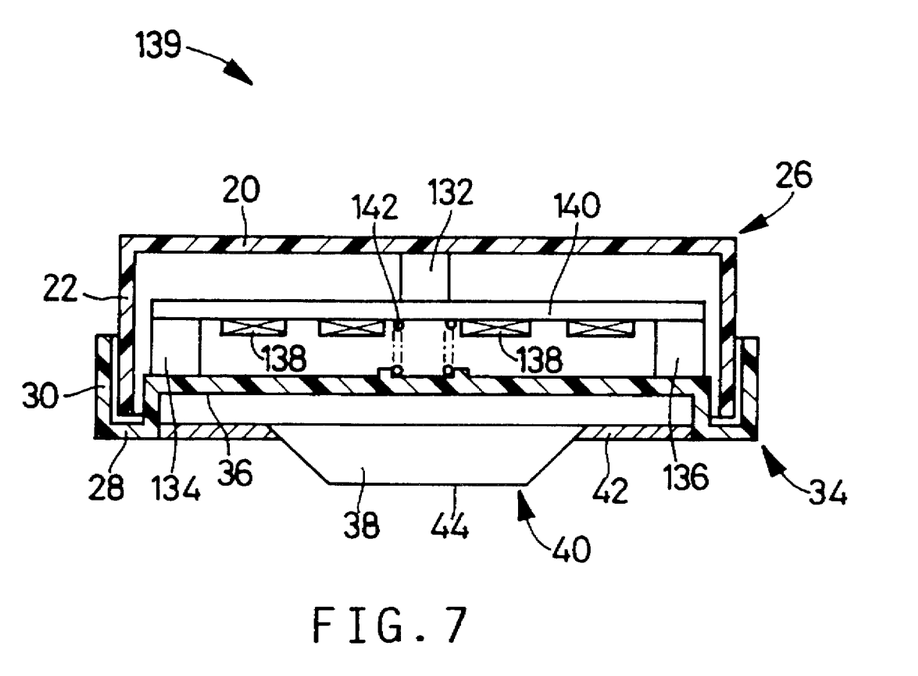
FIG. 7 is a cross-sectional view corresponding to FIG. 2, showing another pulse wave detector probe 139 as a fourth embodiment of the invention.

Referring next to FIG. 7, there is shown a fourth embodiment of the present invention. The fourth embodiment relates to a pulse wave sensor probe (PW probe) 139. The same reference numerals as used in FIGS. 1 to 3 for the PW probe 18 as the first embodiment are used to designate the corresponding elements and parts of the PW probe 139 as the fourth embodiment, and the description of those elements and parts is omitted.

The PW sensor 139 does not have parts corresponding to the intermediate walls 24, 32 of the PW sensor 18, and has a shape memory alloy (SMA) sheet 140 in place of the polymer gel 48 of the PW sensor 18. The SMA sheet 140 is formed of, e.g., a Ni-Ti alloy. The SMA sheet 140 is fixed at a central portion thereof to a first housing 20 via a first fixture 132 having a heat-insulating property, and is fixed at opposite end portions thereof to a second housing 34 via a second and a third fixture 134, 136 each having a heat-insulating property. Peltier modules 138 identical with the elements 138 of the PW sensor probe 125 of FIG. 6 are fixed to a major surface of the SMA sheet 140 which is opposite to the second housing 34. A compression coil spring 142 is provided between the central portion of the SMA sheet 140 and a bottom wall 28 of the second housing 34. While no electric current is supplied to the Peltier modules 138 and therefore the temperature of the SMA sheet 140 is low, the SMA sheet 140 is curved, so that a pulse wave sensor (PW sensor) 40 fixed to the second housing 34 is held in an advanced position thereof away from the first housing 26. When an appropriate amount of electricity is supplied to the Peltier modules 138 and therefore the SMA sheet 140 is heated, the SMA sheet 140 becomes flat while compressing the spring 142, as shown in FIG. 7, so that the PW sensor 40 is held in a retracted position thereof near to the first housing 26. The degree of curvature of the SMA sheet 140 is controllable by changing the amounts of electricity supplied to the Peltier modules 138. Since the second housing 34 and the PW sensor 40 are connected to the opposite end portions of the SMA sheet 140 via the fixture members 134, 136, the PW sensor 40 can be pressed against a superficial temporal artery of a patient with an appropriate pressing force corresponding to the electric current applied to the Peltier modules 138. In the fourth embodiment, too, an actuator provided by the SMA sheet 140, the Peltier modules 138, and the compression coil spring 142 enjoys a small size and a light weight as compared with a conventional air pump, and does not produce operational noise unlike the air pump.

Figure 8:
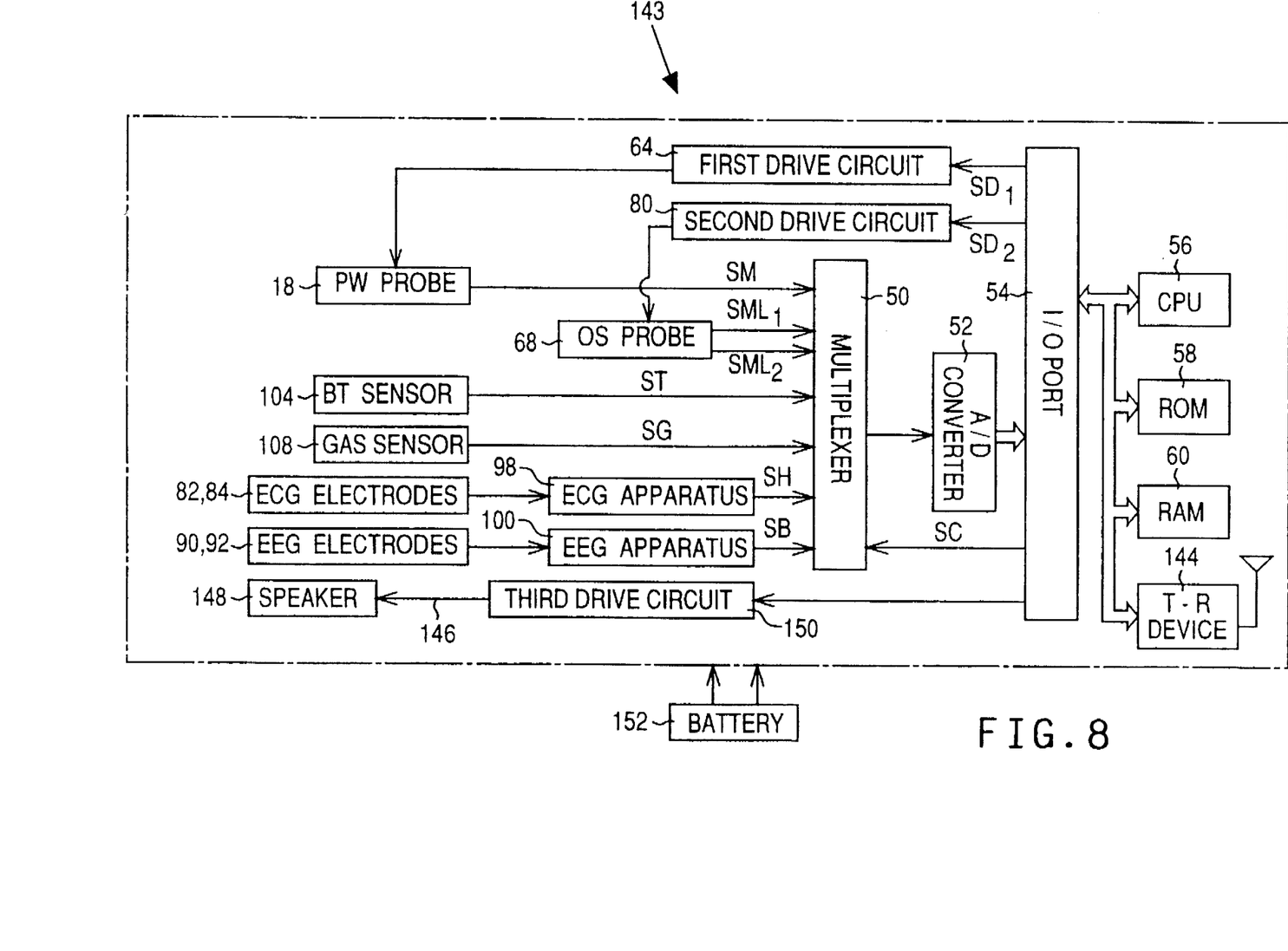
FIG. 8 is a diagrammatic view corresponding to FIG. 3, showing another physical-information monitor system including the pulse wave detector probe 18 shown in FIG. 1.

Referring next to FIG. 8, there is shown a fifth embodiment of the present invention. The fifth embodiment relates to a physical-information monitor system 143 including the pulse wave sensor probe (PW probe) 18 shown in FIGS. 1 to 3. The same reference numerals as used in FIG. 3 are used to designate the corresponding elements and parts of the monitor system 143 as the fifth embodiment, and the description of those elements and parts is omitted.

Although in the first embodiment the PW probe 18 and the other sensors 68, 104, 108, 82, 84, 90, 92 are mounted on the lens frame 10 to monitor the various sorts of physical information of a patient who is undergoing an exercise test, the PW probe 18 and the other sensors 68, 104, 108, 82, 84, 90, 92 may be used to monitor the various sorts of physical information of a patient who is receiving medical treatments at his or her home, without restricting his or her daily activity, and the obtained physical information may be transmitted by radio to a host computer disposed in a hospital. This is achieved by the physical-information monitor system 143 whose electric arrangement is shown in FIG. 8.

The monitor system 143 includes all elements shown in FIG. 3, except for the output device 62, and all of those elements of the monitor system 143 are mounted on, e.g., a resin-based lens frame 10 shown in FIG. 1 to be worn on a patient. The monitor system 143 includes, in place of the output device 62, a signal transmitting and receiving (T-R) device 144 including an antenna, a separator, a modulator, a demodulator, etc. The T-R device 144 is connected to a CPU 56 via a data bus line, and is also mounted on the lens frame 10. Thus, the cable 65 used with the lens frame 10 in the first embodiment is not used with the lens frame 10 in the fifth embodiment. The antenna of the T-R device 144 may be provided in the form of a metal wire which is embedded in a right or left temple 14, 16 of the lens frame 10. A small-sized speaker 148 is connected via a seventh lead wire 146 to the temple 14 or 16 of the lens frame 10, so that the speaker 148 is electrically connected to an I/O port 54 via a third drive circuit 150 also mounted on the lens frame 10. A battery 150 as an electric supply for the monitor system 143 is also mounted on the lens frame 10 to be worn on the patient.

With this arrangement, the various sorts of physical information including the pressure pulse wave represented by the pulse wave signal SM are transmitted from the T-R device 144 to the host computer disposed in the hospital, so that the physical information is displayed on a display device connected to the host computer. If an abnormality of the physical information displayed is identified by a doctor, the doctor can transmit, by radio from the host computer, an instruction signal representing this or her instruction to the patient at his or her home, so that the T-R device 144 of the monitor system 143 receives the instruction signal and the doctor's instruction is output from the speaker 148. In the fifth embodiment, too, the PW probe 18 including a jelly of polymer gel 48 enjoys a small size and a light weight as compared with a conventional air pump, and does not produce, unlike the air pump, operational noise that may disturb the sleeping of the patient.

While the present invention has been described in its preferred embodiments, the invention may otherwise be embodied.

For example, although in the first and fifth embodiments the polymer actuator is provided in the form of a jelly of polymer gel 48, it is possible to employ, as the polymer actuator, a rod or plate of repetitively frozen polyvinylalcohol gel containing polyacrylate. In this case, an electric current is applied to the polymer rod or plate so as to curve the same and thereby pressing the PW sensor 40 against the patient.

While in the first to fifth embodiments the PW probe 18, 113, 125, 139 are mounted on the temple 14, 16 of the lens frame 10 so as to be pressed against the superficial temporal artery of the patient, the PW probe 18, 113, 125, 139 can be adapted to be pressed against other arteries such as a radial artery of the patient, with the same advantages as described above.

Although in the second embodiment the piezoelectric actuator is provided in the form of the stacked piezoelectric ceramic element 114 which is curved because of the slipping deformation of each piezoelectric ceramic layer 116a to 116d, it is possible to use, as the piezoelectric actuator, another type of stacked piezoelectric ceramic element which is obtained by alternately stacking thin ceramic sheets and electrode sheets and which is contracted and expanded in the direction of alternate stacking of the two sorts of sheets.

While in the third or fourth embodiment the bimetal 126 or the shape memory alloy (SMA) sheet 140 is heated and cooled by the Peltier modules 138, it is possible to employ, in place of the Peltier modules 138, one or more heaters each provided on a thin sheet of, e.g., mica. In the latter case, the heaters are fixed to the bimetal 126 or the SMA sheet 140, so that the bimetal 126 or the SMA sheet 140 is heated by supply the heaters with electricity and is cooled by itself by disconnecting the heaters from electric supply.

In each of the illustrated embodiments, it is possible to additionally mount, on the lens frame 10, a glucose sensor for measuring a blood sugar of a patient.

In the fifth embodiment shown in FIG. 8, it is possible that one or two lenses supported by the lens frame 10 be partly or entirely formed of a liquid crystal, so that the liquid crystal can be operated or driven to indicate a message informing a patient wearing the lens frame 10 of an abnormality of the physical information obtained from the patient.

It is to be understood that the present invention may be embodied with other changes, improvements, and modifications that may occur to those skilled in the art without departing from the scope and spirit of the invention defined in the appended claims.

What is claimed is:

1. An apparatus for detecting a pressure pulse wave produced from an arterial vessel of a living subject, comprising:

a pulse wave sensor including at least one pressure sensing element and having a press surface in which said pressure sensing element is provided, said press surface of said pulse wave sensor being adapted to be pressed against said arterial vessel of said subject via a body surface of the subject above the arterial vessel, so that the pressure sensing element detects said pressure pulse wave produced from the arterial vessel;

a support member supporting said pulse wave sensor such that the pulse wave sensor is advanceable away from, and retractable toward, said support member, the support member being adapted to be worn on said subject such that said press surface of the pulse wave sensor is opposed to said body surface of the subject;

an actuator located entirely on the support member provided between said support member and said pulse wave sensor, said actuator deforming, upon application thereto of an electric current, thereby providing a pressing force to press the pulse wave sensor against said arterial vessel of said subject via said body surface of the subject.

2. An apparatus according to claim 1, further comprising a plurality of electrodes provided in contact with said actuator, said electric current being applied to the actuator via said electrodes.

3. An apparatus according to claim 1, wherein said actuator comprises a member selected from the group consisting of a mass of polymer and a piezoelectric element.

4. An apparatus for detecting a pressure pulse wave produced from an arterial vessel of a living subject, comprising:

a pulse wave sensor including at least one pressure sensing element and having a press surface in which said pressure sensing element is provided, said press surface of said pulse wave sensor being adapted to be pressed against said arterial vessel of said subject via a body surface of the subject above the arterial vessel, so that the pressure sensing element detects said pressure pulse wave produced from the arterial vessel;

a support member supporting said pulse wave sensor such that the pulse wave sensor is advanceable away from, and retractable toward, said support member, the support member being adapted to be worn on said subject such that said press surface of the pulse wave sensor is opposed to said body surface of the subject; and a mass of polymer provided between said support member and said pulse wave sensor, said mass of polymer deforming, upon application thereto of an electric current, thereby providing a pressing force to press the pulse wave sensor against said arterial vessel of said subject via said body surface of the subject.

5. An apparatus according to claim 4, wherein said polymer comprises a polymer gel.

6. An apparatus according to claim 5, wherein said polymer gel comprises a jelly of polymethacrylate.

7. An apparatus according to claim 4, wherein said support member comprises:

a first housing;

a second housing to which said pulse wave sensor is fixed; and a flexible diaphragm cooperating with said first and second housings to define a space filled with a jelly of said polymer, so that said jelly of said polymer is deformed upon application thereto of an electric current and accordingly said pulse wave sensor is displaced together with said second housing.

8. An apparatus for detecting a pressure pulse wave produced from an arterial vessel of a living subject, comprising:

a pulse wave sensor including at least one pressure sensing element and having a press surface in which said pressure sensing element is provided, said press surface of said pulse wave sensor being adapted to be pressed against said arterial vessel of said subject via a body surface of the subject above the arterial vessel, so that the pressure sensing element detects said pressure pulse wave produced from the arterial vessel;

a support member supporting said pulse wave sensor such that the pulse wave sensor is advanceable away from, and retractable toward, said support member, the support member being adapted to be worn on said subject such that said press surface of the pulse wave sensor is opposed to said body surface of the subject; and a piezoelectric actuator provided between said support member and said pulse wave sensor, said piezoelectric actuator deforming upon the application thereto of an electric current, thereby providing a pressing force to press the pulse wave sensor against said arterial vessel of said subject via said body surface of the subject.

9. An apparatus according to claim 8, wherein said piezoelectric actuator comprises a stacked piezoelectric ceramic element.

10. An apparatus according to claim 9, wherein said stacked piezoelectric ceramic element is obtained by alternately stacking a plurality of piezoelectric ceramic layers and a plurality of electrode layers, so that the stacked piezoelectric ceramic element is curved upon application of an electric current to said electrode layers and accordingly said pulse wave sensor is displaced.

11. An apparatus for detecting a pressure pulse wave produced from an arterial vessel of a living subject, comprising:

a pulse wave sensor including at least one pressure sensing element and having a press surface in which said pressure sensing element is provided, said press surface of said pulse wave sensor being adapted to be pressed against said arterial vessel of said subject via a body surface of the subject above the arterial vessel, so that the pressure sensing element detects said pressure pulse wave produced from the arterial vessel;

a support member supporting said pulse wave sensor such that the pulse wave sensor is advanceable away from, and retractable toward, said support member, the support member being adapted to be worn on said subject such that said press surface of the pulse wave sensor is opposed to said body surface of the subject; and a bimetal actuator provided between said support member and said pulse wave sensor, said bimetal actuator deforming upon the application thereto of an electric current, thereby providing a pressing force to press the pulse wave sensor against said arterial vessel of said subject via said body surface of the subject.

12. An apparatus according to claim 11, wherein said bimetal actuator comprises a bimetal including two metal sheets which have different coefficients of thermal expansion and are adhered to each other.

13. An apparatus according to claim 12, wherein said bimetal actuator further comprises at least one heater fixed to one of said two metal sheets of said bimetal, so that the bimetal is curved upon heating of said heater and accordingly said pulse wave sensor is displaced.

14. An apparatus for detecting a pressure pulse wave produced from an arterial vessel of a living subject, comprising:

a pulse wave sensor including at least one pressure sensing element and having a press surface in which said pressure sensing element is provided, said press surface of said pulse wave sensor being adapted to be pressed against said arterial vessel of said subject via a body surface of the subject above the arterial vessel, so that the pressure sensing element detects said pressure pulse wave produced from the arterial vessel;

a support member supporting said pulse wave sensor such that the pulse wave sensor is advanceable away from, and retractable toward, said support member, the support member being adapted to be worn on said subject such that said press surface of the pulse wave sensor is opposed to said body surface of the subject; and a shape memory alloy actuator provided between said support member and said pulse wave sensor, said shape memory alloy actuator deforming upon the application thereto of an electric current, thereby providing a pressing force to press the pulse wave sensor against said arterial vessel of said subject via said body surface of the subject.

15. An apparatus according to claim 14, wherein said shape memory alloy actuator comprises a sheet of a shape memory alloy.

16. An apparatus according to claim 15, wherein said shape memory alloy actuator further comprises:

at least one heater which produces heat in response to the application of the electric current fixed to said sheet of said shape memory alloy; and a compression coil spring provided between said sheet of said shape memory alloy being curved and said pulse wave sensor, so that the curved sheet becomes flat while compressing said spring, upon heating of said heater, and accordingly said pulse wave sensor is displaced.

17. An apparatus for detecting a pressure pulse wave produced from an arterial vessel of a living subject, comprising:

a pulse wave sensor including at least one pressure sensing element and having a press surface in which said pressure sensing element is provided, said press surface of said pulse wave sensor being adapted to be pressed against said arterial vessel of said subject via a body surface of the subject above the arterial vessel, so that the pressure sensing element detects said pressure pulse wave produced from the arterial vessel, said pulse wave sensor producing a pulse-wave signal representing the detected pressure pulse wave;

a first signal wire which transmits the pulse-wave signal;

a support member supporting said pulse wave sensor such that the pulse wave sensor is advanceable away from, and retractable toward, said support member, the support member being adapted to be worn on said subject such that said press surface of the pulse wave sensor is opposed to said body surface of the subject, the support member comprising a frame member including two temples which are adapted to be supported by two ears of the subject, respectively, and a front rim which connects between said two temples and which is adapted to be supported by a nose of the subject, wherein the first signal wire is operationally associated with said pulse wave sensor;

at least one physical-information sensor which detects, from the subject, a physical information different from said pressure pulse wave, and produces a physical-information signal representing the detected physical information;

at least one second signal wire which transmits said physical-information signal, said physical information sensor being attached to said frame member via said second signal wire; and an actuator provided between said support member and said pulse wave sensor, said actuator providing a pressing force to press the pulse wave sensor against said arterial vessel of said subject via said body surface of the subject.

18. An apparatus according to claim 17, wherein said first and second signal wires are located in at least one of said two temples or said front rim of said frame member.

19. An apparatus according to claim 18, further comprising a cable connected to a free end of one of said two temples of said frame member which is opposite to the other end of said one temple wherein the other end of said one temple is adjacent to said front rim, wherein said first or second signal wires located in said one of said two temples and said front rim of said frame member enter said cable.

20. An apparatus according to claim 17, wherein said physical-information sensor comprises at least one of a blood oxygen saturation sensor, an electrocardiograph sensor, an electroencephalograph sensor, a body temperature sensor, a carbonic acid gas sensor, and a blood sugar sensor.

21. An apparatus according to claim 17, wherein said actuator comprises a member selected from the group consisting of a mass of polymer, a piezoelectric element, a bimetal, and a shape memory alloy.

* * * * *